United States Patent [19]
Arakawa et al.

[11] Patent Number: 5,603,145
[45] Date of Patent: Feb. 18, 1997

[54] SHEET-FORM HOOK AND FASTENING SYSTEM USING IT

[75] Inventors: Masaaki Arakawa; Kenitirou Arakawa; Masayuki Mizohata, all of Osaka, Japan

[73] Assignee: Nitto Denko Corporation, Osaka, Japan

[21] Appl. No.: 536,203

[22] Filed: Sep. 29, 1995

[30] Foreign Application Priority Data

Sep. 30, 1994 [JP] Japan .................................. 6-237319

[51] Int. Cl.$^6$ .............................. A44B 17/00; A44B 21/00
[52] U.S. Cl. ............................. 24/442; 24/304; 24/306; 602/78
[58] Field of Search ................... 24/442, 306, 304; 604/391, 392; 602/41, 78, 79

[56] References Cited

U.S. PATENT DOCUMENTS

| | | | |
|---|---|---|---|
| 1,921,999 | 8/1933 | Dickinson | 602/78 |
| 1,933,391 | 10/1933 | Reeves | 24/442 |
| 3,036,572 | 5/1962 | Castelli et al. | 602/78 |
| 3,247,847 | 4/1966 | Mathison | 602/78 |
| 3,899,803 | 8/1975 | Brumlik | 24/304 |
| 3,927,443 | 12/1975 | Brumlik | 24/442 |
| 4,169,303 | 10/1979 | Lemelson | 24/204 |
| 5,351,017 | 9/1994 | Yano et al. | 24/304 |

FOREIGN PATENT DOCUMENTS

| | | |
|---|---|---|
| 0352017 | 1/1990 | European Pat. Off. . |
| 0583081 | 2/1994 | European Pat. Off. . |
| 0264418 | 1/1927 | United Kingdom ..................... 602/78 |

*Primary Examiner*—Victor N. Sakran
*Attorney, Agent, or Firm*—Sughrue, Mion, Zinn, Macpeak & Seas

[57] ABSTRACT

A sheet-form hook capable of hooking to a material to be hooked, comprising a sheet-form substrate having thereon at least one projected portion formed by bending at least one piece notched in the substrate to at least one surface side of the substrate, the height of the projected portion from the surface of the substrate being at least 0.3 mm, and a fastening system using the sheet-form hook. The sheet-form hook can be utilized in the field of fastening systems in place of pressure-sensitive adhesive tapes and has a high resistance to staining, which is a weak point of a pressure-sensitive adhesive tape.

7 Claims, 3 Drawing Sheets

SHEET-FORM HOOK AND FASTENING SYSTEM USING IT

FIELD OF THE INVENTION

The present invention relates to a hook having a high resistance to staining, which is a weak point of pressure-sensitive adhesive tapes, and capable of being utilized in the field of a fastening system in place of pressure-sensitive adhesive tapes, and to a fastening system using the hook.

Practically, the sheet-form hook of the present invention can be used for a fastening system of hygienic articles such as fixing of disposable paper diapers, fixing of sanitary towels, etc., medical fixing means such as bandage fixing, etc., and industrial fields such as a field of requiring temporary fixing or re-adhering in the field of using packing tapes, pressure-sensitive adhesive double-sided tapes, etc., (e.g., the fields of automobiles, building materials, etc.). Thus, the sheet-form hook of the present invention can be used in the fields wherein conventional pressure-sensitive adhesive tapes are used.

BACKGROUND OF THE INVENTION

At present, in a fastening system for joining or fixing various kinds of articles, a pressure-sensitive adhesive tape system is mainly used from the points of a cost, a releasable property, a softness, a thinness, etc., but the pressure-sensitive adhesive layer is liable to be stained with various dirts, dusts, etc., and as the case may be, the adhesive force is greatly lowered, whereby the purpose cannot be attained. Practically, a pressure-sensitive adhesive tape is used for a fastening system of paper diapers but in the case of fixing or re-peeling the pressure-sensitive adhesive tape, the finger of a mother comes in contact with the pressure-sensitive adhesive layer, whereby the cream, the talcum powder, etc., attached to the finger stains the pressure-sensitive adhesive layer, and as a result, there is a problem that the adhesive force is lowered to remove or unfasten the diaper.

As a fastening system using such a pressure-sensitive adhesive tape, a hook system is proposed as described in JP-A-3-198802 (the term "JP-A" as used herein means an "unexamined published Japanese patent application") but in the system, since projected portions are formed by printing, pressing out, molding, etc., and the tips of the projected portions are thin like a thread, there is a possibility that the hook system is poor in the sufficient hooking performance and the tips are broken or bend by pressure, whereby the system becomes unusable. Also, the hook system has a problem that the existence of female portions is inevitable and further the system is expensive in the points of the production equipment and working.

SUMMARY OF THE INVENTION

The present invention has been made to overcome those problems.

Accordingly, an object of the present invention is to provide a sheet-form hook which is formed simply at low cost and is excellent in the hooking performance by forming the projected portions by a simple method such as by punching a part of a sheet-form substrate without need of fixing specific projected portions as conventional hooks.

The present invention now provides a sheet-form hook capable of hooking to a material to be hooked, comprising a sheet-form substrate having thereon at least one projected portion formed by bending at least one piece notched in the substrate to at least one surface side thereof, the height of the projected portion from the surface of the substrate being at least 0.3 mm.

The present invention also provides a fastening system using the sheet-form hook.

DETAILED DESCRIPTION OF THE INVENTION

The present invention is described below in more detail based on the accompanying drawings.

Figure 1:
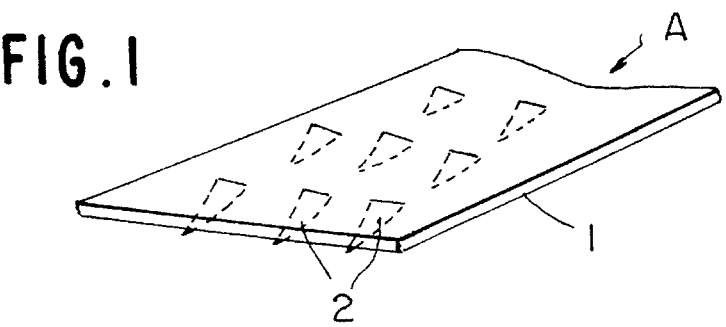
FIG. 1 is a side view showing an embodiment of the sheet-form hook of the present invention.
Figure 2:
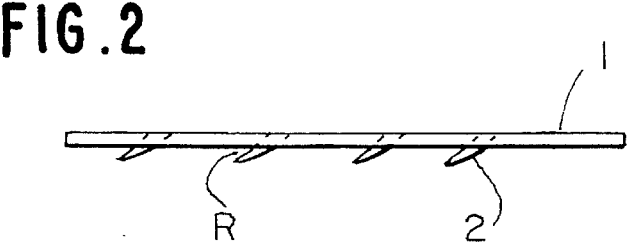
FIG. 2 is a cross sectional view showing the sheet-form hook of the present invention shown in FIG. 1.

FIG. 1 is a slant view showing an embodiment of the sheet-form hook A of the present invention, and FIG. 2 is a cross sectional view of the sheet-form hook shown in FIG. 1. As shown in those figures, a plurality of notches are formed in the sheet-form substrate 1 by punching such as pressing by a cutting edge of an optional form, and each of the notched pieces is bent to one surface side to form a projected portion 2.

In this case, there is no particular restriction on the sheet-form substrate 1 if the substrate has a proper nerve and softness, and for example, there is a material comprising a thermoplastic resin such as polyester series resins, nylon series resins, polyolefin series resins, urethane series resins, vinyl chloride series resins, etc. These resins are used alone or as a blend of them, and also they are used as a monolayer or multilayer sheet-form substrate.

Figure 3:
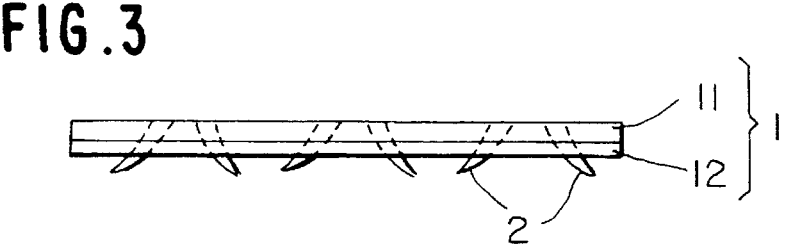
FIG. 3 is a cross sectional view showing another embodiment of the sheet-form hook of the present invention.

FIG. 3 is a cross sectional view showing an embodiment of the sheet-form hook of the present invention, wherein the sheet-form substrate 1 comprises two layers (11 and 12). In the present invention, from the point of the hooking property, it is preferred that the projected portions 2 of the hook comprise a hard (large elastic modulus) plastic, but on the other hand, when the sheet-form hook of the present invention is used for medical purposes or for diapers, the hook comes in contact with the skin, and therefore, it is desirable to employ a material which is tender to the skin. Thus, in the sheet-form hook shown in FIG. 3, by laminating a layer 11 comprising a hard plastic and a layer 12 comprising a soft plastic, elastomer, foam, cloth, nonwoven fabric, etc., the nerve of the whole sheet and the softness of the projected portions can coexist.

Figure 4:
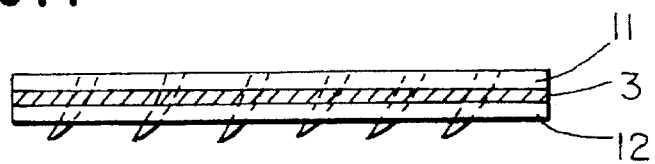
FIG. 4 is a cross sectional view showing still another embodiment of the sheet-form hook of the present invention.

There is no particular restriction on the laminated state but, for example, heat-sealable films are used as the layer 11 and the layer 12, and these films are heat-sealed or the layer 11 and the layer 12 can be laminated via a pressure-sensitive adhesive layer or an adhesive layer 3 as shown in FIG. 4.

Figure 5:
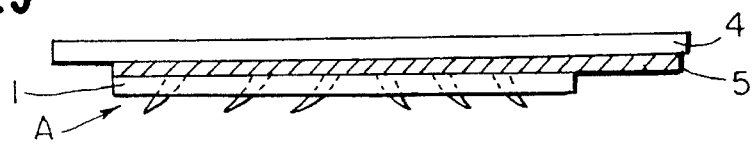
FIG. 5 is a cross sectional view showing a further embodiment of the sheet-form hook of the present invention.

Also, onto the sheet-form substrate 1 can be laminated other substrate 4 via a pressure-sensitive adhesive layer 1 or an adhesive layer 5 as shown in FIG. 5 or they are laminated as they are by heat seal. In particular, in the case of FIG. 5, the sheet-form hook A is laminated on a pressure-sensitive adhesive tape such as an existing diaper tape.

In the present invention, there are no particular restrictions on the form, the size, etc., of the projections 2 bent after notched in the sheet-form substrate 1, but it is preferred that the height thereof from the surface of the substrate is at least 0.3 mm, and preferably from about 0.5 to 2 mm. If the height is too short, there is a possibility that the sheet-form hook applied is detached. Also, it is preferred for making the clue of hooking that the shape of the projected portion 2 is tapered from the base portion thereof to the tip as shown in FIG. 1. For example, it is preferred that the width of the base portion thereof is from about 0.3 to 5 mm and the length is from about 0.5 to 10 mm. Also, there is no particular restriction on the bent angle R from the surface of the substrate, but for example, the bent angle is generally from about 10° to 80°, and preferably from about 30° to 60°. If the bent angle is less than 10°, there is a possibility that the hooking performance becomes insufficient.

Furthermore, there is no particular restriction on the direction of the projected portion 2. For example, the directions of the total projected portions can be in one direction as shown in FIG. 2, the directions thereof can be in random directions or opposite directions each other as shown in FIG. 3, the directions can be in opposite directions in a block form as shown in FIG. 5, or the directions can be in two or more direction (not shown).

When the directions of the projected portions are in two or more directions, since hooking is not in one direction, there is an advantage that when a force is applied to the direction parallel with the direction of the projected portion, the sheet-form hook is difficult to detach as compared with the case of directing the projected portions in one direction.

Figure 6:
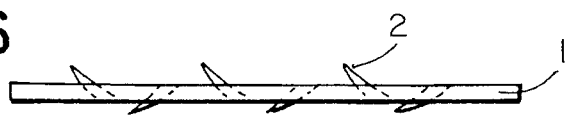
FIG. 6 is a cross sectional view showing other embodiment of the sheet-form hook of the present invention.

Also, the projected directions may be not only in one surface side but also may be in both the surface sides of the substrate as shown in FIG. 6. When the projected portions are in both the surface directions, the sheet-form hook can be used as a double faced hook in place of an existing pressure-sensitive adhesive double-sided tape.

The projected portions in the present invention are obtained by bending to at least one surface side at least one piece, preferably a plurality of pieces notched in the sheet-form substrate. There is no particular restriction on the method of forming many notched pieces. For example, a method of punching with a cutting edge having a desired shape, a method of embossing working, a method of injection molding, and a method of press working can be employed.

In the present invention, projected portions are not formed by fixing special projected portions to a sheet substrate as in a conventional case, but the projected portions are formed by bending the notched pieces formed by punching the sheet substrate itself leaving other portions. Hence, the sheet-form hook of the present invention is obtained very simply and at low cost.

Figure 7:
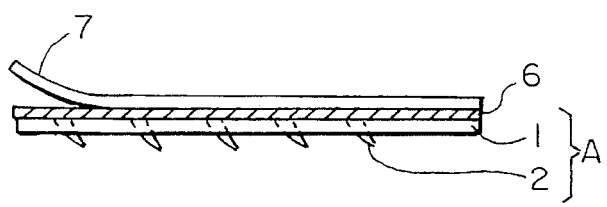
FIG. 7 is a cross sectional view showing still other embodiment of the sheet-form hook of the present invention.

Furthermore, in the present invention, if necessary, a pressure-sensitive adhesive layer 6 is formed on at least one surface of the sheet-form hook A. For example, by forming a pressure-sensitive adhesive layer 6 on a sheet-form substrate 1 at the opposite side to the side having projected portions as shown in FIG. 7, the sheet-form hook A can be fixed to an adherend. Moreover, for protecting the pressure-sensitive adhesive layer 6 before use, a separator 7 can be formed on the layer as shown in FIG. 7.

Figure 8:
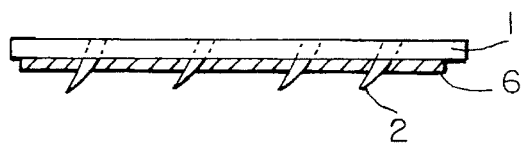
FIG. 8 is a cross sectional view showing a further embodiment of the present invention.
Figure 9:
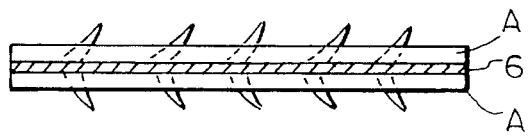
FIG. 9 is a cross sectional view showing another embodiment of the sheet-form hook of the present invention.

As shown in FIG. 8, by forming a pressure-sensitive adhesive layer 6 on a sheet-form substrate 1 at the side having formed projected portions 2, hooking by the hooks and fixing the pressure-sensitive adhesive can be combined. This embodiment is particular suitable when the surface of the female portion (the material to be hooked) or the adherend is rough. As shown in FIG. 9, the back surfaces of sheet-form hooks A, A are adhered to each other with a pressure-sensitive adhesive layer 6 to obtain a double faced sheet-form hook.

The present invention further provides a fastening system wherein the sheet-form hook is hooked to other material to be hooked or the sheet-form hooks are hooked to each other.

Figure 10:
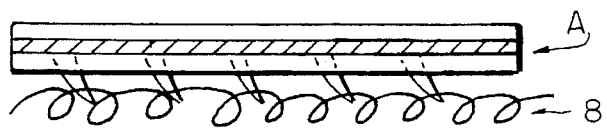
FIG. 10 is a view explaining an embodiment of the fastening system using the sheet-form hook of the present invention.
Figure 11:
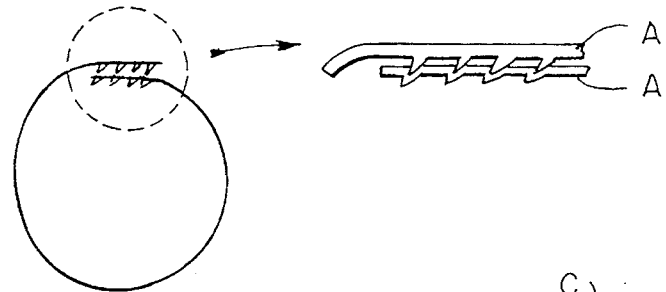
FIG. 11 is a view explaining an embodiment of the using state of the sheet-form hook of the present invention.

For example, as shown in FIG. 10, the sheet-form hook A can be hooked to a material 8 to be hooked having loops, such as a cloth, a nonwoven fabric, and other porous material and fixed. In this case, if the forms of the projected portions of the sheet-form hook are fined, an ordinary nonwoven fabric can be used as the material to be hooked. Also, as shown in FIG. 11, by hooking the sheet-form hooks A,A to each other, the fastening system of the present invention can be obtained.

Figure 12:
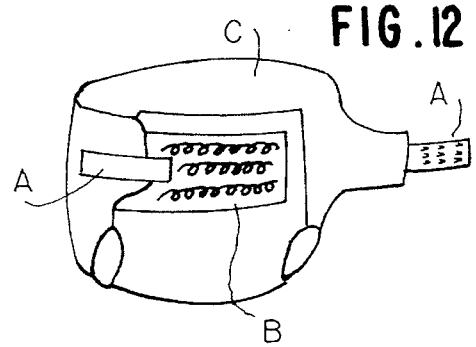
FIG. 12 is a view explaining an embodiment of the using state of the sheet-form hook of the present invention for a paper diaper.
Figure 13:
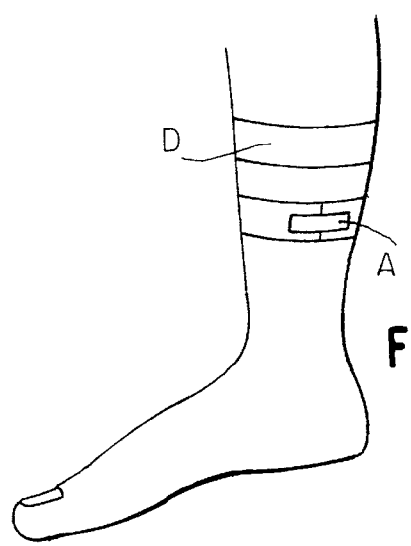
FIG. 13 is a view explaining other embodiment of the using state of the sheet-form hook of the present invention.
Figure 14:
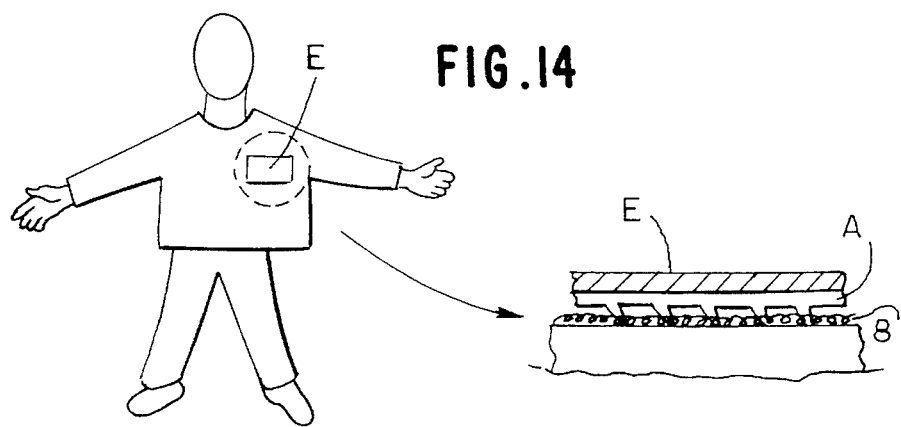
FIG. 14 is a view explaining another embodiment of the using state of the sheet-form hook of the present invention.

The sheet-form hook of the present invention can be, for example, used for fixing a disposable paper diaper as shown in FIG. 12. In FIG. 12, by hooking a sheet-form hook A to a cloth B having loops, a diaper C can be fixed or re-fixed. Also, the sheet-form hook A of the present invention can be used for the fastening system of hygiene articles, such as for fixing sanitary towels, etc. Further, the sheet-form hook can be used as a fixing means for medical purposes, such as for fixing a bandage D, etc., as shown in FIG. 13. The sheet-form hook can also be used for fixing a name card E, a disposable body warmer, etc., as shown in FIG. 14. Furthermore, the sheet-form hook can be used for industrial fields of using conventional pressure-sensitive adhesive tapes, such as the fields (e.g., the fields of automobiles, building materials, etc.) of requiring temporary fixing or re-adhering in the field of using packaging pressure-sensitive adhesive tapes or pressure-sensitive adhesive double-sided tapes.

The present invention is described in more detail by the following examples and comparative examples.

EXAMPLE 1

Many punching workings were applied to a polyester film having a thickness of 38 μm using a cutting edge such that many tapered projections each having a width of 1 mm and a length of 3 mm were formed, and each punched piece was bent to about 60° as shown in FIG. 1 to obtain a sheet-form hook of the present invention. The height of each projected portion was about 1.5 mm.

EXAMPLE 2

By following the same procedure as in Example 1 except that the bent angle of each of the projected portions was 35° and the height of each projected portion was 0.6 mm, a sheet-form hook of the present invention was obtained.

EXAMPLE 3

By following the same procedure as in Example 1 except that the bent angle of each of the projected portions was 8° and the height of each projected portion was 0.6 mm, a sheet-form hook of the present invention was obtained.

COMPARATIVE EXAMPLE 1

By following the same procedure as in Example 1 except that the bent angle of each of the projected portions was 30° and the height of each projected portion was 0.25 mm, a sheet-form hook was obtained.

COMPARATIVE EXAMPLE 2

By coating a styrene series pressure-sensitive adhesive (50 μm thick) on a 38 μm thick polyethylene film, a pressure-sensitive adhesive tape was obtained.

A rubber series pressure-sensitive adhesive was coated on one surface of a blend film (100 μm) of polypropylene/polyethylene (50/50) at a thickness of 60 μm and the sheet-form hook obtained in Example 1 was adhered to the pressure-sensitive adhesive layer surface to form a fastener tape for a diaper. Diapers each using a cloth as the female portion were used by 10 persons and the result was evaluated in the following items. The results are shown in Table 1 below. In addition, the results obtained in the case of using the pressure-sensitive adhesive tape obtained in Comparative Example 2 are shown in Table 1 as a comparison.

TABLE 1

|  | Item 1 | Item 2 | Item 3 |
| --- | --- | --- | --- |
| Example 1 | 0 | 0 | 0 |
| Comparative Example 2 | 0 | Δ | x |

[Item 1]
The fastener tape was fixed to the diaper in an ordinary state.
[Item 2]
The fastener tape was fixed to the diaper in the state that a cream was previously applied to the hand.
[Item 3]
The fastener tape was fixed to the diaper in the state that a talcum powder was previously applied to the hand.
[Evaluation Standard]
0: Ten persons in 10 persons evaluated good.
Δ: Six persons in 10 persons evaluated good.
x: Less than 3 persons in 10 persons evaluated good.

From the results shown above, it can be seen that the fastening system of the present invention has a strong resistance to staining and is more practically used as compared with the conventional pressure-sensitive adhesive tape system.
[Adhesive Force Test]

The adhesive force of each of the sheet-form hooks obtained in Examples 1 to 3 and Comparative Example 1 to a material to be hooked (female portion) was measured by the method shown below, and the results obtained are shown in Table 2 below. In this case, a nylon series cloth having a basis weight of 50 g/m² was used.

TABLE 2

|  | Shearing Adhesive Force (minute) | 180° Peeling Adhesive Force (g/25 mm) |
| --- | --- | --- |
| Example 1 | >120 | 300 |
| Example 2 | 58 | 220 |
| Example 3 | 5 | 25 |
| Comparative Example 1 | 0.5 | 8 |

[Shearing Adhesive Force]
After press-adhering each sheet-form hook to the cloth fixed to a cardboard as the female portion by reciprocating once a roller of 5 kg, a weight of 200 g was hung from the sheet-form hook and the time that the hook was fallen was measured.
[180° Peeling Adhesive Force]
A sample was prepared in the same manner as above, and after press-adhering, the adhesive force at 180° peeling with a tension of 300 meters/minute was measured.

The sheet-form hook of the present invention and the fastening system of the present invention using the sheet-form hook have a high resistance to staining, which is the weak point of conventional pressure-sensitive adhesive tapes, are excellent in the hooking faculty, and can be obtained simply at low cost.

While the invention has been described in detail and with reference to specific embodiments thereof, it will be apparent to one skilled in the art that various changes and modifications can be made therein without departing from the spirit and scope thereof.

What is claimed is:

1. A sheet-form hook capable of hooking to a material to be hooked, said hook comprising a sheet-form substrate having thereon at least one projected portion formed by bending at least one piece notched in the substrate to at least one surface side thereof, said projected portion having a height from the surface of the substrate of at least 0.3 mm and a shape that is tapered from a base portion thereof to its tip, and wherein said substrate is a monolayer film comprising a thermoplastic resin.

2. The sheet-form hook according to claim 1, wherein a pressure-sensitive adhesive layer is formed on at least one surface of the sheet-form substrate.

3. The sheet-form hook according to claim 1, wherein the sheet-form hook is used for a fastening system of hygienic articles.

4. A fastening system comprising a sheet-form hook capable of hooking to a material to be hooked, said hook comprising a sheet-form substrate having thereon at least one projected portion formed by bending at least one piece notched in the substrate to at least one surface side thereof, said projected portion having a height from the surface of the substrate of at least 0.3 mm and a shape that is tapered from a base portion thereof to its tip, and wherein said substrate is a monolayer film comprising a thermoplastic resin.

5. The fastening system of claim 4, wherein said sheet-form hook is hooked to a second sheet-form hook.

6. The fastening system of claim 4, wherein said sheet-form hook is hooked to a material to be hooked.

7. A sheet-form hook capable of hooking to a material to be hooked, said hook comprising a sheet-form substrate having thereon at least one projected portion formed by bending at least one piece notched in the substrate to at least one surface side thereof, said projected portion having a height from the surface of the substrate of at least 0.3 mm and a shape that is tapered from a base portion thereof to its tip, and wherein said substrate is a laminate film comprising a first layer comprising a hard plastic and a second layer comprising a material selected from the group consisting of soft plastic, elastomer, foam, cloth, and nonwoven fabric.

* * * * *